US007754445B2

(12) United States Patent
Casez

(10) Patent No.: US 7,754,445 B2
(45) Date of Patent: Jul. 13, 2010

(54) METHOD FOR THE ENZYMATIC PRODUCTION OF A CURING AGENT AND ITS FLUID STATE

(75) Inventor: Herve Casez, Chatillon D'Azergues (FR)

(73) Assignee: TMI Europe, Vaulx-En-Velin (FR)

( * ) Notice: Subject to any disclaimer, the term of this patent is extended or adjusted under 35 U.S.C. 154(b) by 1552 days.

(21) Appl. No.: 10/477,189

(22) PCT Filed: May 31, 2002

(86) PCT No.: PCT/FR02/01844

§ 371 (c)(1),
(2), (4) Date: Dec. 14, 2004

(87) PCT Pub. No.: WO02/097076

PCT Pub. Date: Dec. 5, 2002

(65) Prior Publication Data

US 2005/0082512 A1    Apr. 21, 2005

(30) Foreign Application Priority Data

May 31, 2001    (FR)    ................................. 01 07344

(51) Int. Cl.
*C12P 1/00*    (2006.01)
*C01B 15/00*    (2006.01)
(52) U.S. Cl. ........................ 435/41; 252/186.1; 424/53; 424/94.4; 423/582; 423/546; 423/366
(58) Field of Classification Search ...................... None
See application file for complete search history.

(56) References Cited

U.S. PATENT DOCUMENTS

| 3,821,083 | A | * | 6/1974 | Van Leemputten et al. .. | 435/176 |
| 4,259,445 | A | * | 3/1981 | Glass et al. .................. | 435/178 |
| 4,320,116 | A | * | 3/1982 | Bjorck ........................ | 424/610 |
| 4,761,380 | A | | 8/1988 | Desmons et al. | |
| 5,043,176 | A | * | 8/1991 | Bycroft et al. ............... | 426/335 |
| 5,116,751 | A | * | 5/1992 | Shinmen et al. ............. | 435/194 |
| 5,206,156 | A | * | 4/1993 | Samain et al. ............... | 435/101 |
| 5,403,450 | A | | 4/1995 | Mellor et al. | |
| 5,614,401 | A | * | 3/1997 | Takahashi et al. ........... | 435/176 |
| 5,733,764 | A | * | 3/1998 | Nielsen ....................... | 435/183 |
| 5,747,078 | A | * | 5/1998 | De Jong et al. .............. | 426/9 |
| 2002/0119136 | A1 | * | 8/2002 | Johansen .................... | 424/94.4 |

FOREIGN PATENT DOCUMENTS

| EP | A1-0 307 376 | 3/1989 |
| EP | 0 397 227 A1 | 11/1990 |
| EP | 0 518 445 A1 | 12/1992 |
| GB | 2 209 523 A | 5/1989 |
| JP | 58-152486 | 9/1983 |
| JP | 04021627 | * 1/1992 |
| WO | WO 87/07838 | 12/1987 |
| WO | WO 96/38548 | 12/1996 |

OTHER PUBLICATIONS

Pruitt et al. 1985. The lactoperoxidase system. Chemistry and biological significance. Chapter 8. Biochemistry of peroxidase system: antimicrobial effects. p. 143-178.*
About Coagulation and Flocculation. http://www.waterspecialists.biz/html/about_coagulation_flocculati.html. p. 1-2.*
Siragusa et al. 1989.Inhibition of Listeria monocytogenes Growth by the Lactoperoxidase-Thiocyanate-H2O2 Antimicrobial System. Applied and environmental microbiology. 55(11):2802-2805.*
Liang et al. 2000. Biomedical Application of Immobilized Enzymes. J Pharm Sci 89: 979-990.*
Salt et al. 1995. Selective flocculation of cellular contaminants from soluble proteins using polyethyleneimine: A study of several organisms and polymer molecular weights. Enzyme and Microbial Technology 17:107-113.*
Sigma-Aldrich. 2009. Peroxidase Enzymes. http://www.sigmaaldrich.com/life-science/metabolomics/enzyme-explorer/analytical-enzymes/peroxidase-enzymes.html. p. 1-5.*
Pruitt M. K. et al., University of Oxford, John Radcliffe Hospital, *Biochemiestry of Peroxidase System: Antimicrobial Effects*; pp. 143-178 (1985).
Marshall M.E. V., *J of General Microbiology*; vol. 120; pp. 513-516; 1980.
Moreno M. et al.; *Laboratire de Genie Biochimique, Institut National des Sciences Appliquees*; pp. 483-488; 1979.

* cited by examiner

*Primary Examiner*—Taeyoon Kim
(74) *Attorney, Agent, or Firm*—Oliff & Berridge, PLC

(57) ABSTRACT

The invention relates to a method for the enzymatic production of a curing agent in its fluid state, e.g. liquid, comprising, in free phase, at least one oxygenated chemical species. Said method consists in bringing into contact at least one enzymatic catalysts agent, comprising at lease one peroxidase-type enzyme; an oxidizable substrate in aqueous phase that can be oxidized by the action of an oxygen donor, by catalysis by said enzymatic catalysis agent, generating said oxygenated chemical species in free phase; and said oxygen donor. The inventive method is characterized in that: e) an aqueous reaction bath is formed comprising, in addition to the oxidizable substrate and the oxygen donor, said enzymatic catalysis agent in divided solid phase, but in free phase, distributed is said bath, which may be set in motion; f) the aqueous reaction bath is separated into a fraction enriched with the enzymatic catalysis agent in divided solid phase and a fraction free from said catalysis agent, from which the curing agent is obtained.

19 Claims, 3 Drawing Sheets

METHOD FOR THE ENZYMATIC PRODUCTION OF A CURING AGENT AND ITS FLUID STATE

Figure 1:
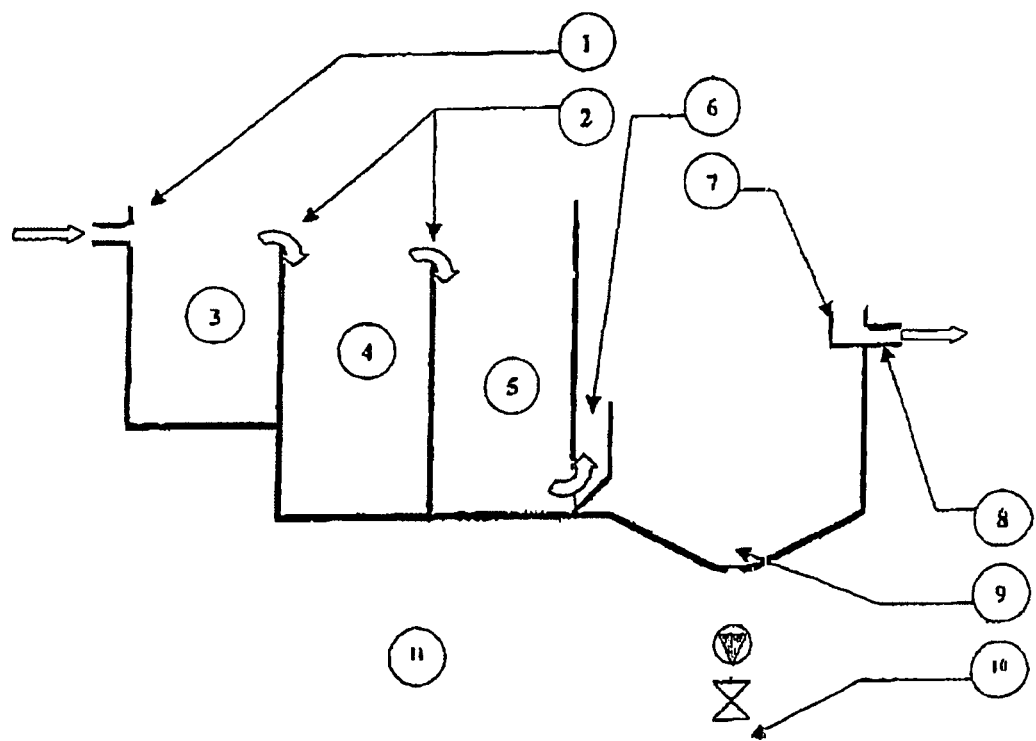

The present invention relates to generating a concentrated and continuous flow, in liquid phase, of oxygenated chemical species and oxidized substrates, thereby making it possible to obtain solutions which can be used, for example, for washing, decontaminating and sterilizing different alimentary products, including water, and also industrial materials, as well as for depolluting and purifying fluids and for preparing alimentary, pharmaceutical and cosmetic products.

The use of natural antimicrobial enzyme systems, such as the oxidoreductases, for example the lactoperoxidase system, for this purpose is known and a large number of applications have been described.

The properties of this enzyme system have been studied, in particular, in "The lactoperoxidase system chemistry and biological significance" (1985) Marcel Dekker, Inc, New York, Chap. 8 pp 143-178.

In outline, this lactoperoxidase/thiocyanate/hydrogen peroxide antimicrobial system comprises three components:
- an enzyme: lactoperoxidase,
- an oxidizable substrate: the thiocyanate ion ($SCN^-$)
- an oxygen donor: hydrogen peroxide.

In this system, and in liquid medium, the lactoperoxidase catalyses the thiocyanate oxidation reaction.

In the presence of a sufficient quantity of hydrogen peroxide and under the correct pH conditions, the oxidation reaction continues towards oxyacid derivatives which are even more oxidized.

In a non-limiting manner, the oxygenated chemical species which are obtained, either on their own or in a mixture, are the hypothiocyanite ion $OSCN^-$, the $O_2SCN^-$ and $O_3SCN^-$ ions, the superoxide $O_2^-$ and trioxide $O_3^-$ an ions, the hydroxyl ion $OH^-$, nitric oxide NO, dinitrogen trioxide $N_2O_3$, nitrogen dioxide $NO_2$, peroxynitrite $ONO_2$, hydroperoxynitrile $ONHO_2$, sulfur dioxide $SO_2$, sulfur trioxide $SO_3$, sulfurous acid $HSO_3$ and hypochlorous acid HOCl.

The abovementioned oxygenated chemical species are known to have bacteriostatic and bactericidal effects, in particular in regard to a large number of microorganisms such as bacteria, for example the Pseudomonae, the Enterobacteriaceae, such as *E. coli, Salmonella*, the *Listeria* or *Campylobacter*, sporulated forms and protozoa, viruses, yeasts or fungi.

As a result of the action of the oxygenated chemical species obtained, in particular the oxidized thiocyanate ions such as $OSCN^-$, $O_2SCN^-$ and $O_3SCN^-$, which are able to interact with the components of cell membranes or to oxidize chemical pollutants, this antimicrobial system can also be used for decontamination.

In the presence of a hydrogen peroxide-supplying substrate, which can be hydrogen peroxide itself or, for example, a metal peroxide or a supplementary enzyme system which produces hydrogen peroxide, with this supplementary enzyme system being, for example, an oxidoreductase together with an oxidizable substrate and oxygen, such as the glucose/glucose oxidase system in aqueous medium, it is possible to use the complete system and, in outline, the reaction properties of such an antimicrobial system comprise three steps:
- the production of hydrogen peroxide by the hydrogen peroxide supplier,
- the thiocyanate oxidation reaction,
- decontamination by the action of the oxygenated chemical species obtained.

A large number of applications are described.

For example, WO-A-8707838 describes a process for packaging, in dry form, an antibacterial composition containing lactoperoxidase, thiocyanate and a native oxygen donor with a view to its subsequent use.

U.S. Pat. No. 5,403,450 discloses the use of units in which oxidoreductases are immobilized for the purpose of converting substances which are capable of being oxidized and which are present as pollutants in water.

JP58152486 teaches, for example, the immobilization of enzymes on polymer particles for repeated use.

Systems for immobilizing enzymes or enzyme systems on reactor walls or on films, beads and other supports comprising a substantial specific area are also known.

However, none of these uses is satisfactory due to the excessive consumption of enzymes which they entail:
- either due to their packaging, for example in dry form, which involves a use by powdering the products to be treated, and therefore quantities of enzyme which are proportional to the areas and to the volumes of products to be treated,
- or due to the low reaction yields of the immobilized enzymes,
- or due to the rapid breakdown of the oxygenated chemical species which are generated.

The process according to the invention makes it possible to solve all the abovementioned drawbacks by making it possible to produce a treatment agent in the fluid, for example liquid, state, which agent comprises, in the free state, at least one stable oxygenated chemical species with high yield and exhibiting substantial endurance.

The invention relates to:

a process for enzymically producing a treatment agent in the fluid, for example liquid, state, comprising, in the free state, at least one oxygenated chemical species, by bringing into contact at least:
- one agent of enzymic catalysis, comprising at least one enzyme of the peroxidase type,
- and one substrate which can be oxidized in aqueous phase and which is capable of being oxidized by the action of an oxygen donor, by means of catalysis by said agent of enzymic catalysis, thereby generating said oxygenated chemical species in the free state,
- said oxygen donor, according to which:
a) an aqueous reaction bath is formed, which bath comprises, in addition to the oxidizable substrate and the oxygen donor, said agent of enzymic catalysis in the solid and divided phase, but in the free state, which agent is distributed in said bath, which latter may possibly be set in motion,
b) the aqueous reaction bath is separated into a fraction which is enriched in agent of enzymic catalysis in solid and divided phase and into a fraction which lacks said agent of catalysis and from which the treatment agent is obtained.

The oxygen donor is preferably a peroxide such as hydrogen peroxide.

An oxygenated chemical species in the free state is understood as being a chemical species in the ionic state whose dissociation constant, at the pH of the resulting solution, displaces the equilibrium of the dissociation reaction towards the existence, in the free state, of said oxygenated chemical species.

The invention affords the following variants:

the oxidizable substrate, possibly in aqueous phase, is introduced into the aqueous reaction bath.

the agent of enzymic catalysis, in the state of a solid and divided phase or in liquid phase, is introduced into the reaction bath.

the agent of enzymic catalysis is discharged from the reaction bath.

the process is performed continuously or discontinuously.

aggregates of solid particles, which are inert vis-á-vis the agent of enzymic catalysis, are formed in the aqueous reaction bath, with said aggregates comprising or incorporating, in the free state, said agent of catalysis, and said aggregates being distributed in the aqueous reaction bath and by means of which the said bath is separated, during step (b), into a fraction which is enriched in aggregate and a fraction which is devoid of aggregate and from which the treatment agent is obtained.

the aggregates are floccules and a flocculating agent, for example an anionic or cationic flocculating agent, is introduced into the reaction bath.

the aggregates are coagulates and a coagulating agent is introduced into the reaction bath.

a thickening agent is introduced into the bath.

the agent of enzymic catalysis in solid phase is suspended in the reaction bath, in emulsion form, and, where appropriate, an emulsifying agent is introduced into said bath.

the agent of catalysis comprises a microorganism which is expressing at least one enzyme of the peroxidase type.

a pH-correcting agent is introduced into the bath.

an oxygen donor in the form of a supplementary enzyme system which produces hydrogen peroxide is introduced into the bath and the agent of enzymic catalysis comprises, in addition to the enzyme of the peroxidase type, an enzyme of the oxidoreductase type.

An aggregate is understood as being any formulation which makes it possible to maintain the agent of enzymic catalysis in solid and divided phase, but in the free state, in the reaction medium by means of adding coagulant, flocculant or emulsifier, in the presence or absence of a thickener, but which makes it possible to isolate them from said reaction medium at the end or the reaction and to recycle them.

The free state is understood as meaning a state of suspension in the aggregates without the formation of an ionic or covalent bond between the agent of catalysis and said aggregating agents.

In one implementation variant, the aggregates are floccules.

Floccules are understood as meaning any aggregate of particles which are chemically inert vis-á-vis the enzyme or the enzymic system and which contain said enzyme without immobilizing it, which aggregate can be obtained by adding a cationic or anionic flocculant, after coagulation or without preliminary coagulation, and which is incorporated with or without a pH-correcting agent.

The flocculants which are used are selected from polymeric an ionic or cationic flocculants, such as polysaccharides, anionic heteropolysaccharides or polyacrylamines.

Advantageously, the flocculant's are added to the reaction medium in proportions varying from $0.1 \ 10^{-6}$ to 10 g/l of reaction medium.

In one implementation variant, the aggregates are coagulates.

A coagulate is understood as meaning any aggregate of particles which are inert vis-á-vis the enzyme or the enzyme system and which contain said enzyme without immobilizing it, which aggregate can be obtained by adding a coagulating agent as previously defined.

Advantageously, the coagulants are added to the reaction medium in proportions varying from $0.1 \ 10^{-6}$ to 10 g/l of reaction medium.

The aggregates can be formed by consecutively adding a coagulant and a flocculant; in this way, a coagulation step precedes the flocculation step.

When the flocculation step is preceded by a coagulation step, the latter is effected by introducing a coagulating agent which is selected, for example, from the salts of aluminum or iron, such as: aluminum sulfate, aluminum chloride, sodium aluminate, aluminum polyhydroxychloride, aluminum polyhydroxysulfate, aluminum polyhydroxychlorosulfate, basic aluminum poly-chlorosulfate, aluminum polyhydroxychlorosilicate, aluminum fluorosulfate, ferrous sulfate, ferric sulfate, ferric chloride, ferric chlorosulfate, soda or homopolymers of dimethyldiallylammonium chloride.

The invention also relates to a group of reagents for enzymically producing a treatment agent in the fluid state which comprises, in the free state, at least one oxygenated chemical species, which furthermore comprises an agent of enzymic catalysis and an aggregating agent in aqueous phase and/or a flocculating agent in aqueous phase and/or a coagulating agent in aqueous phase.

In one embodiment, an organic or inorganic thickening agent, which is chemically compatible with the aggregate type which it is desired to use, is added to the mixture.

According to the implementation variants, this thickening agent is introduced into the bath at the same time as introducing the agent of enzymic catalysis or after the aqueous reaction bath has been formed.

This thickening agent is selected from clays, kaolin, silica or silicates or any other compatible inorganic agent which promotes entrainment of the enzyme.

Advantageously, the thickening agent is added to the reaction medium in proportions varying from 0.1 to 100 g/l of reaction medium.

The invention also relates to a group of reagents in unhydrated form for enzymically producing a treatment agent in the fluid state which comprises, in the free state, at least one oxygenated chemical species, which comprises at least one agent of enzymic catalysis and a thickening agent.

Advantageously, the group of reagents in unhydrated form comprises from 0.005 to 10% of agent of enzymic catalysis and from 90 to 99.995% of thickening agent, for example from 5 g to 400 g of lactoperoxidase in dry form and from 1000 g to 5000 g of clay for a reactor having a serviceable volume of 2 $m^3$.

The group of reagents is employed by introducing it into the reactor at the rate of from 0.2 to 10 g/l of serviceable volume.

In another embodiment, an emulsifying agent is added to the mixture.

Emulsion is understood as meaning any suspension which contains an enzyme without immobilizing it and which can be obtained by adding emulsifiers such as fats or soybean lecithin or hydrocarbons.

In particular embodiments, the pH of the aggregate dispersion medium can be stabilized or corrected by adding a pH-correcting agent which will be selected from inorganic or organic acids or bases.

The agents of enzymic catalysis are enzymes which are free, chemically isolated or associated among themselves and which are obtained from isolated microorganisms, cells of vegetable or animal origins or polymicrobial flora. They are, in particular, peroxidases and any natural, selected or genetically modified microorganism which produces enzymes or generates enzymic activity.

The peroxidases which can be used in the present invention comprise peroxidases of vegetable origin, such as horseradish peroxidase or soybean peroxidase, or cereal NADPH nitrate oxidoreductase, or of animal or human origin, such as saliva peroxidase, lactoperoxidase, myeloperoxidase and eosinophil peroxidase.

These peroxidases can be extracted and/or isolated from natural substances such as milk or saliva or be produced using natural or chemical processes which are well known to the skilled person. These peroxidases can also be produced by means of recombinant techniques, with these latter also being well known to the skilled person.

The agents of enzymic catalysis are preferably selected from peroxidases.

In a preferred embodiment, the peroxidase is a lactoperoxidase.

Advantageously, the enzymes are added to the reaction medium in proportions varying from 0.02 to 10 g/l of reaction medium.

The oxidizable substrates are selected from the group consisting of negatively charged halogens and their derivatives and negatively charged pseudohalogens and their derivatives. In this present case, the term negatively charged halogen refers to certain chemical elements in the form of anions which belong to Group VII of the Periodic Table of the Elements and which are, for example, bromides, $Br^-$, chlorides, $Cl^-$ or iodides, $I^-$.

The pseudohalogens are, for example, selected from the group consisting of thiocyanate ions, bisulfite ions, hydrosulfite ions, metabisulfite ions and nitrite and/or hypochlorite ions.

The oxidizable substrates will be selected, by preference and in accordance with the peroxidase employed, from sodium thiocyanate (NASCN) or potassium thiocyanate (KSCN), sodium bisulfite ($NaHSO_3$), sodium hydrosulfite ($Na_2S_2O_4$), sodium metabisulfite ($Na_2S_2O_5$), sodium nitrite ($NaNO_2$) or potassium nitrite ($KNO_2$), sodium hypochlorite (NaOCl) and potassium iodide (KI).

For example, if the peroxidase is:

a saliva peroxidase, either thiocyanate ions or iodide ions and/or their mixtures will be used as the oxidizable substrate, a lactoperoxidase, either thiocyanate ions or iodide ions and/or their mixtures will be used as the oxidizable substrate, a myeloperoxidase, either thiocyanate ions or iodide ions or chloride ions and/or their mixtures will be used as the oxidizable substrate, a horseradish peroxidase, either chloride ions or iodide ions and/or their mixtures will be used as the oxidizable substrate, a peroxidase of vegetable origin, either thiocyanate ions or bromide ions or chloride ions and/or their mixtures will be used as the oxidizable substrate.

In the presence of peroxide, for example oxygen peroxide, the action of these enzyme systems results in the production, in particular, of hypothiocyanite ions or hypohalide ions.

Advantageously, the combined enzyme substrates are added to the reaction medium in proportions varying from 0.05 mM to 15 mM per liter of reaction medium.

The oxygen donor according to the present invention can be hydrogen peroxide or any inorganic peroxide such as the metal peroxides, for example magnesium peroxide or sodium peroxide, or organic peroxides, such as benzyl peroxide, or urea peroxide, but also peracetic acid, potassium permanganate and the percarbonates. In a general manner, any chemical compound which is capable of producing hydrogen peroxide can be used.

Advantageously, the oxygen donors are added to the reaction medium in proportions varying from 0.05 mM to 15 mM per liter of reaction medium.

When the oxygen donor is in the form of a supplementary enzyme system which produces oxygen peroxide, it comprises an oxidizable substrate and an enzyme, for example of the oxidoreductase type, which is specific for this substrate. Thus, when the enzyme systems employed are oxidoreductases, an oxidizable substrate, alone or in combination, with this substrate being selected from substances such as glucose, lactose or xanthine, is added to the medium in order to effect the step of producing the hydrogen peroxide.

The following enzyme systems will be mentioned by way of example: glucose oxidase/glucose, galactose oxidase/galactose, urate oxidase/urate, choline oxidase/choline, glycine oxidase/glycine, glutamate oxidase/glutamate and alcohol oxidase/alcohol.

In the presence of oxygen and water, these enzyme systems are able to produce hydrogen peroxide, which will then be used as oxygen donor in the enzyme system of the process according to the invention.

Alternatively, this oxygen donor can be selected from microorganisms, such as *Streptococcus* and/or *Lactobacillus*, which are able to produce hydrogen peroxide.

The peroxidases and/or oxidoreductases which are employed and which may be mentioned by way of example are:

enzymes of vegetable origin such as horseradish peroxidase (E.C. No. 1.11.1.7) or soybean peroxidase, or cereal NADPH nitrate oxidoreductase (E.C. No. 1.6.6.1), enzymes of fungal origin, such as glucose oxidase (E.C. No. 1.1.3.4), catalase (E.C. No. 1.11.1.6), betagalactosidase (E.C. No. 3.2.1.23) and *Aspergillus* NADPH nitrate oxidoreductase (E.C. No. 1.6.6.2), enzymes of bacterial origin, such as *Enterococcus* NADH peroxidase (E.C. No. 11.1.1), *Vibrio* NADPH oxidoreductase (E.C. No. 1.6.99.3), *Colibacillus* nitrate reductase (E.C. No. 1.9.6.1), *Pediococcus* lactic dismutase oxidase (E.C. No. 1.1.3.2), *Colibacillus* superoxide dismutase (E.C. No. 1.15.1.1), *Arthromyces* peroxidase (E.C. No. 1.11.1.1) and *Colibacillus* betagalactosidase (E.C. No. 3.2.1.23), enzymes of animal origin, such as milk xanthine oxidase (E.C. No. 1.1.3.22), milk lactoperoxidase (E.C. No. 1.11.1.7), leucocyte myeloperoxidase (E.C. No. 1.11.1.7), nervous tissue nitric oxide synthetase (E.C. No. 1.14.13.39), erythrocyte super-oxide dismutase (E.C. No. 1.15.1.1) and hepatocyte sulfite oxidase (E.C. No. 1.8.3.1).

Implementation of step b) of the process according to the invention, that is to say the step of separating the aqueous reaction bath into a fraction which is enriched in agent of enzymic catalysis in solid and divided phase and a fraction which is devoid of said agent of catalysis and from which said treatment agent is obtained, is effected by means of separating and recovering the aggregates or the emulsions. The means which are used and which will be mentioned by way of example are the means which are classically used such as decantation, flotation and centrifugation, in the case of emulsions, and sedimentation, frontal or tangential filtration or a centrifugation, in the case of flocculates or coagulates, and/or cyclonic separation.

The process according to the invention makes it possible to obtain a treatment agent in the fluid, for example liquid, state, which agent comprises, in the free state, at least one stable oxygenated chemical species.

More specifically, the stable oxygenated chemical species is the hypothiocyanite ion ($OSCN^-$).

The invention also relates to a treatment agent in the fluid, for example liquid, state, which agent comprises, in the free state, at least one oxygenated chemical species which is stable for more than 10 hours.

It relates, more specifically, to a treatment agent in the fluid, for example, liquid state which comprises, in the free state, at least the hypothiocyanite ion, which is stable for more than 10 hours.

The process according to the invention makes it possible to produce large quantities of treatment agent solution according to the invention, which solution possesses biocidal properties which can be used for cleaning, washing and disinfecting materials, machines, implements, textiles, containers and pipework and agroindustrial premises and plants or hospitals and care centers. The process also makes it possible to prepare solutions which are intended for formulating cosmetic and pharmaceutical products which are intended for human and/or animal health and alimentary products.

The process also makes it possible to produce washing solutions for decontaminating the surfaces of alimentary products such as fruit, vegetables and leaves, and also animal products.

These biocidal solutions will be able to be used by means of bathing, spraying, injection or nebulization.

It will also be possible to use these solutions as constituents of a product mixture, for example water for reconstituting fruit juice following dehydration or concentration.

The process also makes it possible to sterilize and purify water which is intended for producing water for beverages for human or animal consumption, or thermal spring water, swimming pool water or bath water.

The process according to the invention also makes it possible to treat polluted water, wastewater or industrial effluents and, indeed, gaseous effluents, by circulating them in the liquid.

The chemical contaminants, for example nitrates or phosphates, are thus oxidized, as are the organic pollutants; it will be possible for the breakdown to be total or partial, depending on the flowrate and the concentrations of oxidoreductase.

The implementation of the process according to the invention, that is to say a process for enzymatically producing a treatment agent in the fluid, for example liquid, state, which agent comprises, in the free state, at least one oxygenated chemical species, by bringing into contact at least one agent of enzymic catalysis, comprising at least one enzyme of the peroxidase type, an oxygen donor and a substrate which is capable of being oxidized by said agent of enzymic catalysis, thereby generating said oxygenated chemical species in the free state, is effected in a reactor (FIG. 1) which consists of a compartmentalized tank, which can be closed partially or completely, which is made of metal or a synthetic material and which is provided with a loading aperture (1) and overflows and/or partitions in the form of siphons, permitting passage from one compartment to the next (2).

The reactor according to the invention is made up of three or four compartments, two or three of which are stirred continuously:

the first (3) is intended to receive the agent of enzymic catalysis and optionally the coagulant and the thickening agent; it is stirred at high speed, the second (4) optionally receives the flocculant and optionally receives the pH-correcting agent; it is stirred at low speed, the third, which is supplied with oxidizable substrate as well as oxygen donor, is the site of the desired enzyme reaction and is also stirred slowly, in the fourth compartment, the aqueous reaction bath is separated, into a fraction which is enriched with agent of enzymic catalysis in solid and divided phase and a fraction which is devoid of said agent of catalysis and from which said treatment agent is obtained, on a lamellar sedimentor which comprises a low supply point (6), an overflow (7) which is connected to the outlet, which is located just below the water stream (8), and a low point for dynamically extracting the sedimented solid matter (9) with a view to discharging it (10) or recovering it with a view to recycling (11).

In an implementation variant, the process according to the invention, that is to say a process for enzymically producing a treatment agent in the fluid, for example liquid, state, which agent comprises, in the free state, at least one oxygenated chemical species, is implemented, by bringing into contact at least one agent of enzymic catalysis, comprising at least one enzyme of the peroxidase type, an oxygen donor and an oxidizable substrate, which is capable of being oxidized by said agent of enzymic catalysis, thereby generating said oxygenated chemical species in the free state, in a reactor (FIG. 2) which consists of a compartmentalized tank, which can be partially or completely closed, which is made of metal or of a synthetic material, and which is provided with a loading aperture (1) of overflows permitting passage from one compartment to another, and which comprises three compartments, the first two of which are stirred continuously.

The first, into which the agent of enzymic catalysis and the emulsifying agent are introduced, is stirred rapidly, the second, to which the oxidizable substrate is supplied and which is the site of the desired enzymic reaction, is stirred at low speed;

the third compartment is a recovery vat (5) which enables the emulsion, of the solution comprising at least one oxygenated chemical species in the free state and residual substrates, to be continuously pumped toward a separation unit, which can be a coalescer, a flotator, a centrifuge (6), a filter or a cyclone.

Applying the process according to the invention to the production of a solution of oxygenated chemical species in solution, by means of using lactoperoxidase, in flocculate form, in the presence of from 0.2 to 0.5 mM $H_2O_2$ and from 0.4 to 1 mM KSCN, results in an aqueous solution which contains between 0.05 and 0.35 mM of oxygenated chemical species.

When used for washing and decontaminating lettuces by means of consecutive sprays and baths at 10° C., this solution enables the population of bacterial contaminants, such as *Pseudomonas* bacteria ($10^5$ cfu/ml) to be reduced significantly (from 2 to 5 logs on average), and *Listeria* bacteria ($10^5$ cfu/ml) to be reduced significantly by from 1 to 2 logs, as compared with untreated control lettuces, with a contact time of the order of 10 minutes.

EXAMPLES

Figure 2:
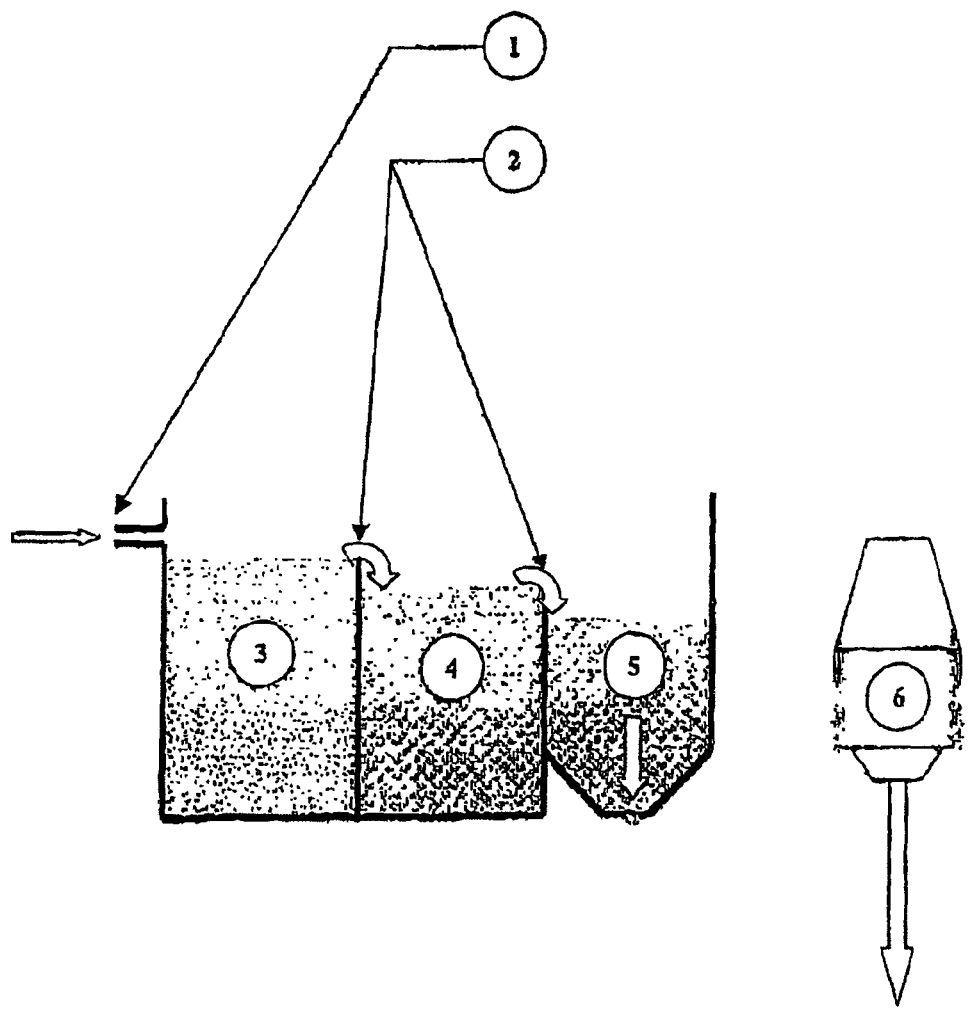

In a reactor such as that described in FIG. 2, 0.25 g/l lactoperoxidase are introduced at the same time as 10 g/l clay and 0.55 ml of coagulant, while variable quantities of KSCN and $H_2O_2$, as shown in Table 1 below, are introduced following stirring and passage into the reaction compartment.

TABLE 1

|  | 1 | 2 | 3 | 4 |
| --- | --- | --- | --- | --- |
| KSCN (mM) | 0.5 | 0.6 | 0.7 | 0.8 |
| $H_2O_2$ (mM) | 0.3 | 0.4 | 0.5 | 0.6 |

Following reaction, samples are removed for measuring enzymic activity and the resulting level of free chemical species.

The hypothiocyanite ions (OSCN⁻) are able to react with the sulfhydryl groups of a 5,5'-dithiobis (2-nitrobenzoic acid) molecule which has previously been reduced in the presence of an excess of sodium borohydride.

This reduced molecule absorbs light at a wavelength of 412 nm.

When the hypothiocyanite ions (OSCN⁻) oxidize the sulfhydryl groups, the absorbance at 412 nm decreases in proportion to the quantity of ions which are present in the sample, thereby enabling them to be quantified.

The thiocyanate ion (SCN⁻) is able to react with FeCl3 in acid medium in order to form a colored product the quantity of which is proportional to that of the thiocyanate present and can be measured by photometry at a wavelength of 450 nm.

In order to measure the quantity of thiocyanate which is present in a sample, it is necessary to produce a calibration range.

TABLE 2

|   |   | 1 | 2 | 3 | 4 |
|---|---|---|---|---|---|
| OSCN⁻ | $\Delta OD_{412nm}$ | $0.855^{1/2}$ | $0.999^{1/2}$ | $1.250^{1/2}$ | $1.320^{1/2}$ |
|  | [OSCN] mM | 0.190 | 0.220 | 0.275 | 0.290 |
| Initial SCN⁻ | $OD_{412nm}$ | 0.242 | 0.252 | 0.279 | 0.310 |
|  | [SCN⁻] mM | 0.67 | 0.70 | 0.77 | 0.86 |
| Residual SCN⁻ | $OD_{412nm}$ | 0.184 | 0.186 | 0.210 | 0.237 |
|  | [SCN⁻] mM | 0.51 | 0.52 | 0.58 | 0.66 |
|  | pH | 6.66 | 6.62 | 6.63 | 6.59 |
| Coagulation quality |  | 3/5 | 3/5 | 3/5 | 2.5/5 |

The initial enzyme activity in the reactor is checked in assay No. 4.

This is done using 50 μl of coagulate and corresponds to:

$\Delta OD_{405nm}/10 \text{ seconds} = 1.023$

The enzyme activity I measured by colorimetry at 405 nm using a chlorogenic substrate, i.e. 2,2'-azino-bis or ABTS.

Lactoperoxidase catalyses the oxidation of the ABTS in the presence of hydrogen peroxide. The oxidized ABTS molecule has the property of absorbing at 405 nm, thereby making it possible to measure the activity of an enzyme solution by following the quantity of oxidized ABTS which is produced (proportional to the $OD_{405nm}$ in accordance with the Beer-Lambert law) per unit of time, with the absorbance being measured continuously at 405 nm.

Monitoring the Stability of the Solution.

Figure 3:
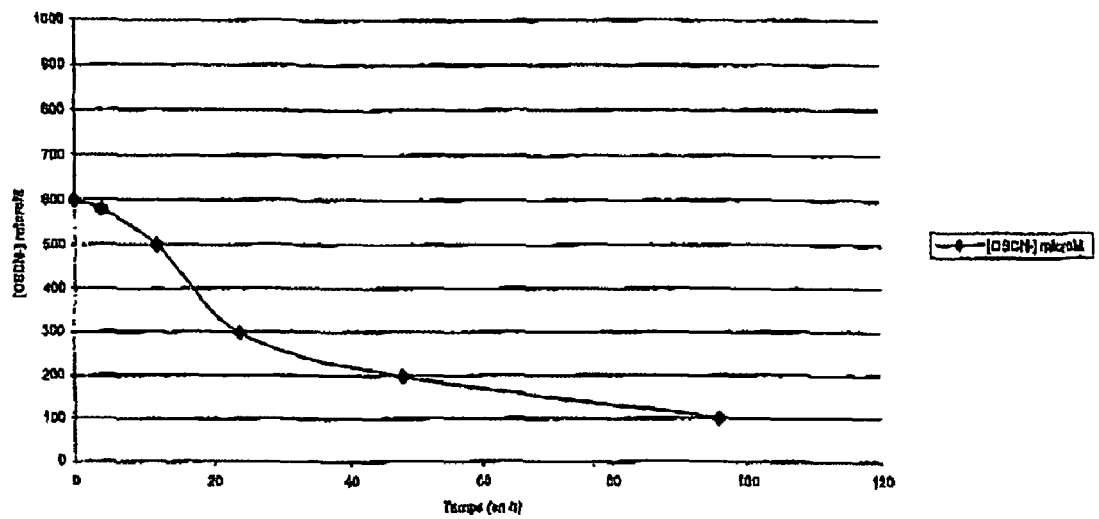
Figure 4:
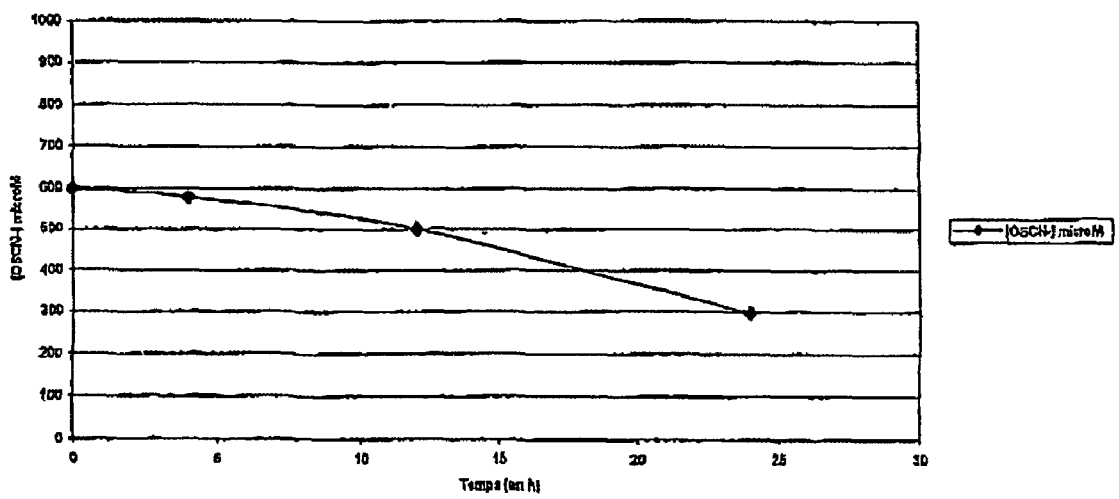

The methods described above are used to monitor the change in the concentration of hypothiocyanite ion, i.e. OSCN⁻, in solutions leaving the reactor, the results of which are obtained are illustrated in FIGS. 3 and 4, which depict the curve for the changes in the concentration of hypothiocyanite ion, OSCN⁻, in the water leaving the reactor over a period of 1 day (FIGS. 4) and 4 days (FIG. 3).

The results which are obtained show (see FIG. 4) that the concentration of OSCN⁻ changes from 600 mM to 500 mM after 10 hours and that its concentration has only fallen by 50% after 20 hours.

Over a period of 4 days, a curve is obtained (see FIG. 3) which shows, after 80 hours, a residual concentration of hypothiocyanite ion, OSCN⁻, which is equal to 16% of the initial concentration

The invention claimed is:

1. A process for enzymatically producing a treatment agent in a fluid state that lacks an enzymatic catalyst, the treatment agent comprising at least one oxygenated chemical species in a free state, by bringing into contact in an aqueous reaction bath a mixture comprising:

an enzymatic catalyst comprising a peroxidase;
a flocculating agent selected from the group consisting of polysaccharides, anionic heteropolysaccharides and polyacrylamines, and/or a coagulating agent selected from the group consisting of salts of aluminum and salts of iron;
an oxygen donor; and
a substrate;
the process comprising:
a) forming aggregates of solid particles that are inert to the enzymatic catalyst, wherein the aggregates comprise or incorporate the enzymatic catalyst, and the aggregates are distributed in the aqueous reaction bath, wherein the enzymatic catalyst is in a solid and divided phase, but in a free state, in the aqueous reaction bath;
b) generating an oxygenated chemical species in the free state by allowing the enzymatic catalyst to catalyze oxidation of the substrate by the oxygen donor; and
c) separating the aqueous reaction bath into a first fraction enriched with the enzymatic catalyst in the solid and divided phase, and a second fraction that lacks the enzymatic catalyst and contains the treatment agent, wherein the first fraction is enriched with the aggregates, and the second fraction is devoid of the aggregates.

2. The process as claimed in claim 1, wherein the enzymatic catalyst is introduced into the reaction bath, in the solid and divided phase.

3. The process as claimed in claim 1, wherein the enzymatic catalyst is introduced into the reaction bath as a solid and divided form entrained in a liquid phase.

4. The process as claimed in claim 1, wherein the oxidizable substrate is introduced into the aqueous reaction bath as an aqueous phase.

5. The process as claimed in claim 1, wherein the oxygen donor is introduced into the aqueous reaction bath as an aqueous phase.

6. The process as claimed in claim 1, wherein, following the separation step (c), the enzymatic catalyst is discharged from the aqueous reaction bath.

7. The process as claimed in claim 1, wherein said process is performed continuously or discontinuously.

8. The process as claimed in claim 1, wherein the enzymatic catalyst is suspended, in solid phase, in the aqueous reaction bath in the form of an emulsion and an emulsifying agent is introduced into said bath.

9. The process as claimed in claim 1, wherein, during step (a), a thickening agent is introduced into the aqueous reaction bath.

10. The process as claimed in claim 9, wherein the thickening agent is selected from clays, kaolin, silica or silicates.

11. The process as claimed in claim 1, wherein a pH-correcting agent is introduced into the bath.

12. The process as claimed in claim 1, wherein an oxygen donor in the form of a supplementary enzyme system which produces hydrogen peroxide is introduced into the bath and the enzymatic catalyst further comprises an oxidoreductase.

13. The process as claimed in claim 1, wherein the peroxidase is a lactoperoxidase.

14. The process as claimed in claim 1, wherein the oxidizable substrate is selected from the group consisting of sodium thiocyanate (NaSCN), potassium thiocyanate (KSCN), sodium bisulfite (NaHSO₃), sodium hydrosulfite (Na₂S₂O₄), sodium metabisulfite ($Na_2S_2O_5$), sodium nitrite ($NaNO_2$), potassium nitrite ($KNO_2$), sodium hypochlorite (NaOCl) and potassium iodide (KI).

15. The process as claimed in claim 1, wherein the oxygen donor is hydrogen peroxide.

16. A process for enzymatically producing a treatment agent in a fluid state that lacks an enzymatic catalyst, the treatment agent comprising at least one oxygenated chemical species in a free state, the process comprising:
   a) bringing into contact in an aqueous reaction bath a mixture comprising:
   an enzymatic catalyst comprising a peroxidase, wherein the enzymatic catalyst is in a solid and divided phase, but in a free state, in the aqueous reaction bath;
   a flocculating agent selected from the group consisting of polysaccharides, anionic heteropolysaccharides and polyacrylamines, and/or a coagulating agent selected from the group consisting of salts of aluminum and salts of iron;
   an oxygen donor; and
   a substrate;
   b) generating an oxygenated chemical species in the free state by allowing the enzymatic catalyst to catalyze oxidation of the substrate by the oxygen donor; and
   c) separating the aqueous reaction bath into a first fraction enriched with the enzymatic catalyst in the solid and divided phase, and a second fraction that lacks the enzymatic catalyst and contains the treatment agent,
   wherein the process is carried out in a reactor comprising four compartments, wherein two or three of said compartments are stirred continuously, the process comprising:
   i) receiving in a first compartment the enzymatic catalyst and the coagulating agent and optionally a thickening agent, and stirring the first compartment at a first speed;
   ii) in a second compartment, optionally receiving the flocculant and optionally receiving a pH-correcting agent, and stirring the second compartment at a second speed, wherein the second speed is slower than the first speed;
   iii) receiving in a third compartment the oxidizable substrate and the oxygen donor, and stirring the third compartment at a third speed, wherein the third speed is slower than the first speed; and
   iv) in a fourth compartment, separating the aqueous reaction bath into said first fraction enriched with the enzymatic catalyst in solid and divided phase, and said second fraction that contains the treatment agent and is devoid of the enzymatic catalyst; wherein the aqueous bath is separated by a technique selected from the group consisting of decantation, flotation, centrifugation, filtration and cyclonic separation.

17. The process as claimed in claim 1, wherein the second fraction is used to decontaminate the surfaces of alimentary products.

18. The process as claimed in claim 1, wherein the coagulating agent is selected from the group consisting of aluminum sulfate, aluminum chloride, sodium aluminate, aluminum polyhydroxychloride, aluminum polyhydroxysulfate, aluminum polyhydroxychlorosulfate, basic aluminum polychlorosulfate, aluminum polyhydroxychlorosilicate, aluminum fluorosulfate, ferrous sulfate, ferric sulfate, ferric chloride and ferric chlorosulfate.

19. The process as claimed in claim 16, wherein the coagulating agent is selected from the group consisting of aluminum sulfate, aluminum chloride, sodium aluminate, aluminum polyhydroxychloride, aluminum polyhydroxysulfate, aluminum polyhydroxychlorosulfate, basic aluminum polychlorosulfate, aluminum polyhydroxychlorosilicate, aluminum fluorosulfate, ferrous sulfate, ferric sulfate, ferric chloride and ferric chlorosulfate.

* * * * *